Feb. 6, 1968 F. W. ANDERSON Plant Pat. 2,794
NECTARINE TREE
Filed Sept. 23, 1966
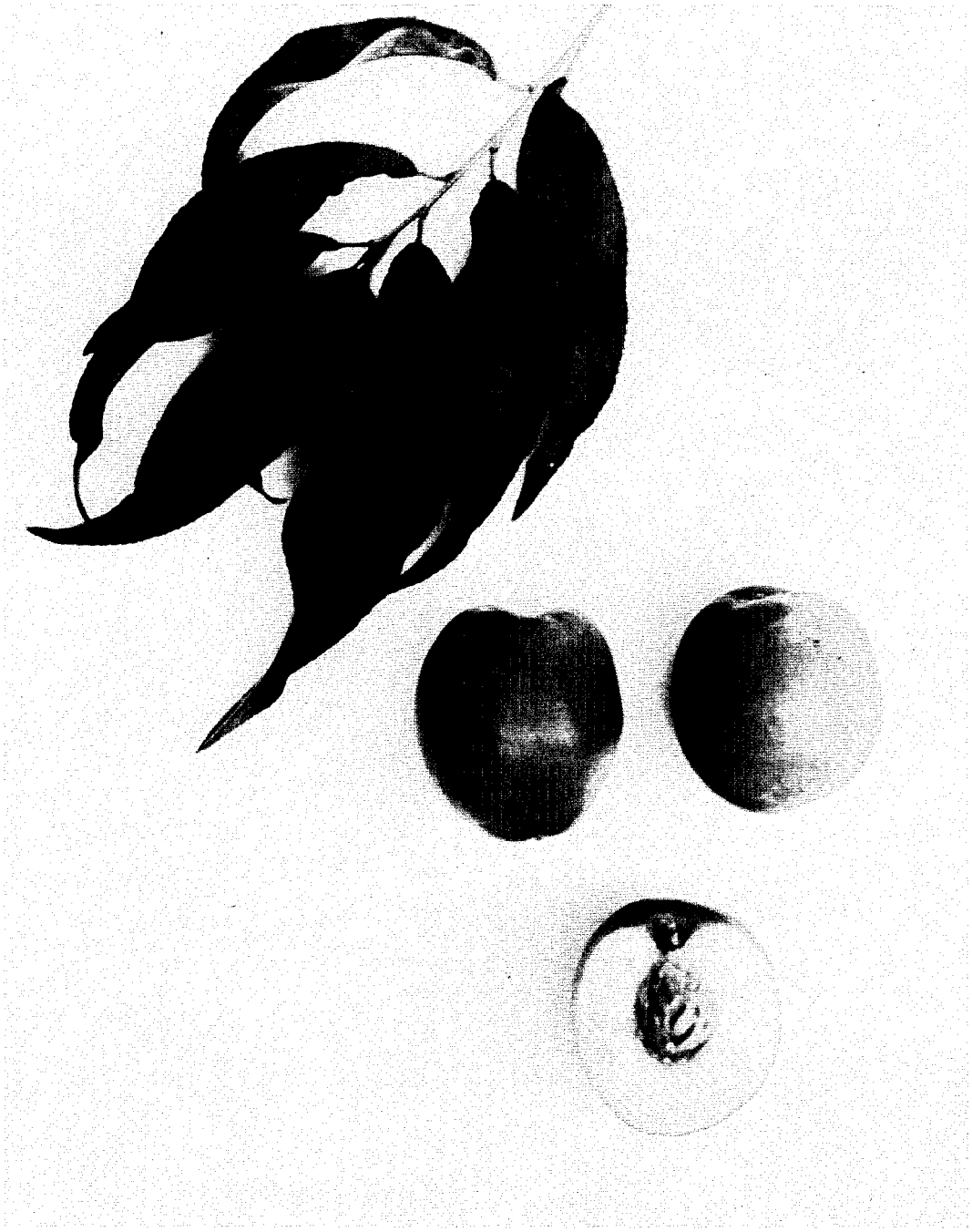
INVENTOR
Frederic W. Anderson
BY
Webster & Webster
ATTORNEYS United States Patent Office Plant Pat. 2,794
Patented Feb. 6, 1968

2,794
NECTARINE TREE

Frederic W. Anderson, Merced, Calif., assignor, by mesne assignments, to Reedley Nursery, Inc., Reedley, Calif.

Filed Sept. 23, 1966, Ser. No. 581,664
1 Claim. (Cl. Plt.—41)

This invention relates to a new and distinct variety of nectarine tree which is a regular and productive bearer of large, yellow-flesh freestone fruit having yellow skin overspread with red; the variety being embraced by group 112 (with a sweet kernel) in the classification established by Caillavet and Souty in their Monographie des Principales Variétés de Pêchers, 1950 edition.

The present variety of nectarine tree is essentially characterized, as to novelty, by early ripening of the fruit for harvest; such ripening occurring approximately ten days earlier than the Grand River (United States Plant Patent No. 1,248) and Sunrise (United States Plant Patent No. 1,256) nectarines, and almost three weeks earlier than the John Rivers (unpatented) nectarine.

The present variety of nectarine tree is further characterized, as to novelty, by fruit which when ripe has a substantially complete overspreading of the red on the yellow ground color of the skin; the fruit—in form—being globose to oblong.

The herein claimed variety of nectarine tree was originated by me as a second generation seedling of a Red Grand nectarine (United States Plant Patent No. 1,060) × Early Sun Grand (United States Plant Patent No. 1,420); such origination of the variety having been accomplished by me, under conditions of close observation, in my experimental orchard located near Le Grand, Merced County, Calif.

Subsequent to origination of the variety, and recognition by me of its novel and distinctive characteristics, I asexually reproduced it in my experimental orchard located as aforesaid, by top-working on orchard trees. Such asexual reproductions were found to run true to the original tree in all respects.

The drawing is an illustration, by photographic reproduction in color, of a twig with leaves, two whole fruit, and one-half of another fruit cut to show the flesh and with the stone remaining in place.

Referring now more specifically to the pomological details of this new and distinct variety of nectarine tree, the following is an outline description thereof; all major color plate identifications, by comparison with fresh specimens, being by reference to Maerz and Paul Dictionary of Color.

Tree:
- *Size.*—Medium.
- *Vigor.*—Vigorous.
- *Growth.*—Spreading.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium.
- *Lenticels.*—Number—medium.

Leaves:
- *Size.*—Medium to large. Average length—5½" to 6". Average width—1⅛" to 1⅜".

- *Form.*—Lanceolate; acutely pointed.
- *Thickness.*—Medium.
- *Texture.*—Smooth.
- *Margin.*—Crenate.
- *Petiole.*—Medium length.
- *Glands.*—Average number—4. Size—medium. Form reniform. Position—usually 2 on petiole and 1–3 on blade.
- *Stipules.*—None.
- *Color.*—Top side—Medium Green (23–L–9). Under side—Lighter Green (22–L–6).

Flower buds:
- *Size.*—Medium.
- *Length.*—Medium.

Flowers:
- *Blooming period.*—Date of first bloom—Mar. 5, 1966. Date of full bloom—Mar. 15, 1966. Medium, as compared with other varieties.
- *Size.*—Large.

Fruit:
- *Maturity when described.*—Eating to hard ripe—June 10, 1966.
- *Date of first picking.*—May 30, 1966.
- *Date of last picking.*—June 10, 1966.
- *Size.*—Uniform; large. Average diameter axially—2½". Average transversely in suture plane—2⅜"–2½".
- *Form.*—Uniform; symmetrical; globose to oblong.
- *Suture.*—Distinct. Shallow, with slight depression beyond pistil point.
- *Ventral surface.*—Rounded slightly.
- *Cavity.*—Rounded. Depth—medium. Breadth— medium.
- *Apex.*—Short.

Skin:
- *Thickness.*—Medium to thick.
- *Texture.*—Medium to tough.
- *Tendency to crack.*—None.
- *Down.*—Wanting.
- *Color.*—Yellow (11–L–6) ground color substantially completely overspread with Red (4–L–4 to 5–L–6).

Flesh:
- *Amygdalin.*—Wanting.
- *Juice.*—Rich.
- *Texture.*—Medium firm; meaty.
- *Fibers.*—Few.
- *Ripens.*—Evenly.
- *Flavor.*—Subacid.
- *Aroma.*—Distinct to wanting.
- *Eating quality.*—Good to best.
- *Color.*—Yellow (9–K–4) when shipping hard, shading to Golden Yellow (10–L–6) when eating ripe.

Stone:
- *Type.*—Free when eating ripe; retains short fiber-like threads along ridges.
- *Size.*—Medium to large. Average length—1⅜". Average breadth—1". Average thickness—¾".
- *Form.*—Oblong to oval.
- *Sides.*—Equal.
- *Ridges.*—Rounded.
- *Pits.*—Angular.
- *Tendency to split.*—Slight.
- *Kernel.*—Sweet, with good flavor.
- *Color.*—Light Tan (12–I–6).

Use: Market; dessert.
Keeping quality: Good.
Shipping quality: Good.

The tree and its fruit herein described may vary in slight detail due to climatic and soil conditions under which the variety may be grown; the present description being of the variety as grown in the Central Valley of California.

The following is claimed:

1. A new and distinct variety of nectarine tree, substantially as illustrated and described, characterized by large, globose to oblong, early ripening, freestone fruit having yellow flesh, and yellow skin substantially completely overspread with red; the fruit ripening approximately ten days earlier than the Grand River and Sunrise nectarines, and almost three weeks earlier than the John Rivers nectarine.

No references cited.

ROBERT E. BAGWILL, *Primary Examiner.*